(12) United States Patent
Drake, Jr.

(10) Patent No.: US 6,711,954 B2
(45) Date of Patent: Mar. 30, 2004

(54) METHOD AND APPARATUS FOR IMPROVING THE DYNAMIC RANGE OF LASER DETECTED ULTRASOUND IN ATTENUATIVE MATERIALS

(75) Inventor: Thomas E. Drake, Jr., Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 09/766,180

(22) Filed: Jan. 19, 2001

(65) Prior Publication Data

US 2003/0029243 A1 Feb. 13, 2003

(51) Int. Cl.[7] .............................. G01N 9/18; G01B 9/02
(52) U.S. Cl. .............................. 73/655; 73/643; 73/657; 356/345; 356/359; 356/432
(58) Field of Search .......................... 73/655, 657, 597, 73/598, 602, 643, 644; 356/359, 432, 345, 432 T; 359/279

(56) References Cited

U.S. PATENT DOCUMENTS

| | | | |
|---|---|---|---|
| 4,121,469 A | 10/1978 | Kaule et al. | 73/643 |
| 4,291,950 A | 9/1981 | Pepper et al. | 359/252 |
| 4,513,384 A | 4/1985 | Rosencwaig | 364/563 |
| 4,572,949 A * | 2/1986 | Bowers et al. | 250/227 |
| 4,633,715 A * | 1/1987 | Monchalin | 73/657 |
| 4,659,224 A * | 4/1987 | Monchalin | 356/352 |
| 4,966,459 A | 10/1990 | Monchalin | 356/358 |
| 5,035,144 A | 7/1991 | Aussel | 73/602 |
| 5,131,748 A | 7/1992 | Monchalin et al. | 356/349 |
| 5,285,261 A | 2/1994 | Dumoulin | 356/432 |
| 5,347,392 A * | 9/1994 | Chen et al. | 359/279 |
| 5,402,235 A * | 3/1995 | Monchalin | 356/357 |
| 5,408,480 A * | 4/1995 | Hemmati | 372/10 |
| 5,520,052 A * | 5/1996 | Pechersky | 73/579 |
| 5,608,166 A | 3/1997 | Monchalin et al. | 73/657 |
| 5,615,675 A | 4/1997 | O'Donnell et al. | 128/653.1 |
| 5,619,326 A * | 4/1997 | Takamatsu et al. | 356/357 |
| 5,672,830 A | 9/1997 | Rogers et al. | 73/597 |
| 5,723,773 A | 3/1998 | Bryan | 73/61.75 |
| 5,734,470 A | 3/1998 | Rogers et al. | 356/354 |
| 5,814,730 A * | 9/1998 | Brodeur et al. | 73/597 |
| 5,824,908 A | 10/1998 | Schindel et al. | 73/632 |
| 5,900,935 A * | 5/1999 | Klein et al. | 356/347 |
| 6,008,887 A * | 12/1999 | Klein et al. | 356/28.5 |
| 6,115,127 A | 9/2000 | Brodeur et al. | 356/357 |
| 6,122,060 A * | 9/2000 | Drake, Jr. | 356/359 |
| 6,128,081 A | 10/2000 | White et al. | 356/357 |
| 6,288,529 B1 * | 9/2001 | Takeuchi et al. | 324/76.22 |

FOREIGN PATENT DOCUMENTS

| | | | |
|---|---|---|---|
| EP | 0097473 A1 | 4/1985 | |
| EP | 0629838 A2 | 12/1994 | |
| EP | 0763192 A1 | 12/1996 | |
| EP | 1127255 A1 | 5/2000 | |
| FR | 2 656 478 | 12/1989 | H04B/10/00 |

* cited by examiner

Primary Examiner—Hezron Williams
Assistant Examiner—Jacques Saint-Surin
(74) Attorney, Agent, or Firm—Koestner Bertani, LLP

(57) ABSTRACT

A system for identifying ultrasonic displacements in a material under test utilizing a time-varying output pulse of a first laser beam. The system includes a seed laser light source for providing a laser beam, a modulating assembly in the path of propagation of the laser beam for time-varying of the laser beam, at least one optical isolation assembly placed in the path of propagation of the laser beam for preventing reflected laser light feedback into the seed laser light source, and at least one laser light amplification assembly placed in the path of propagation of the laser beam for amplifying the laser beam which passes the amplified time-varying output pulse of the laser beam.

25 Claims, 3 Drawing Sheets

METHOD AND APPARATUS FOR IMPROVING THE DYNAMIC RANGE OF LASER DETECTED ULTRASOUND IN ATTENUATIVE MATERIALS

TECHNICAL FIELD OF THE INVENTION

The present invention relates generally to a field of optical information processing and more particularly to a method and system for detecting ultrasonic displacements in a material under test utilizing a time-varying output pulse of a laser beam.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in the manufacturing processes. Specifically, non-destructive evaluation ("NDE") methods are required to assess the structural integrity of composite structures, for example, to detect inclusions, de-laminations and porosities. Conventional NDE methods, however, are very slow, labor-intensive, and costly. As a result, testing procedures adversely increase the manufacturing costs associated with composite structures.

Various systems and techniques have been proposed to assess the structural integrity of composite structures. One method to generate and detect ultrasound using lasers discloses the use of a first modulated, pulsed laser beam for generating ultrasound on a work piece and a second pulsed laser beam for detecting the ultrasound. Phase modulated light from the second laser beam is then demodulated to obtain a signal representative of the ultrasonic motion at the surface of the work piece.

Another method to generate and detect ultrasound using lasers discloses the use of a laser to detect deformations of a oscillatory or transient nature on a material under test surface. The deformations on the material under test surface can be produced by an ultrasound wave or other excitation. Light from the laser is scattered by the deformations, some of which light is collected by collecting optics and transmitted via a fiber optic to a beam splitter which deflects a small portion of the collected light to a reference detector and delivers the remaining portion of the light to a confocal Fabry-Perot interferometer, which generates an output signal indicative of the deformations on the material under test surface. The reference detector measures the intensity of the scattered laser light at the input of the interferometer to generate a reference signal. A stabilization detector measures the intensity of the scattered laser light at the output of the interferometer to generate a prestabilization signal. The ratio of the reference signal to the prestabilization signal is used to generate a final stabilization signal which drives a piezoelectric pusher inside the interferometer to adjust its resonant frequency.

The advanced composite structures often attenuate ultrasound within the composite materials. It would be desirable to have a system capable of expanding the dynamic range of ultrasound detection in an attenuative material such as advanced composites.

The above-referenced methods attempt to reduce the noise associated with the detection schemes. However, the methods disclosed do not explore expanding and improving the dynamic range of ultrasound detection in attenuative materials.

Therefore, there is a need has arisen for a method and system of ultrasonic laser detection that overcomes the disadvantages and deficiencies of the prior art. Namely, such a system should be able to extend the dynamic range of ultrasound detection in an attenuative material.

SUMMARY OF THE INVENTION

The present invention provides a method and system for detecting ultrasonic displacements at a remote target under test utilizing a laser beam that substantially eliminates or reduces disadvantages and problems associated with previously developed ultrasonic detection systems.

More specifically, the present invention provides a system for detecting ultrasonic displacements at a remote target with a laser beam having a time dependent pulse profile. The system and method for improving the dynamic range of laser detected ultrasonic in attenuative materials includes a seed laser light source. This laser source produces a laser which is modulated by an assembly placed in the laser beam's path. The modulated laser has a time-dependent pulse profile. Ultrasonics at the remote target further modulate, reflect and/or scatter the laser beam to produce phase-modulated light. Optics collect this phase modulated light. An interferometer coupled to the collection optics demodulates the phase-modulated light and provide an output signal representative of the ultrasonics at the remote target.

A processor may be utilized to process output signal of the interferometer to obtain data representative of the ultrasonics.

Another embodiment of the present invention involves matching the time-dependent pulse profile of the detection laser beam to the attenuative properties of the remote target. Alternatively, the time-dependent pulse profile may be varied to increase the signal strength of the detected ultrasonics.

The present invention provides an important technical advantage by extending the dynamic range of a Laser UT system. Previous systems would synchronize the generation of the ultrasonic event with the peak of the detection laser to maximize signal-noise-ratio without regard for potential dynamic range improvements based on exploiting non-uniform illumination profiles, while the present invention provides that the use of time-dependent detection laser illumination profiles can be used to both optimize signal-noise-ratio and extend the dynamic range of the Laser UT systems.

Another technical advantage of the present invention is an extended dynamic range with which to detect ultrasound in the material under test and improved signal-to-noise ratio due to the time-varying pulse profiles of the detection laser.

Yet another technical advantage of the present invention is the ability to use a detection laser with lower output power. This allows the use of smaller collection optics and optical scanners. Additionally, the use of a lower power detection laser reduces the total power applied to the material under test and damage of the material under test.

Stored energy in amplifier can be extracted in an optimum way to match the properties of the material under test.

BRIEF DESCRIPTION OF THE DRAWINGS

For a more complete understanding of the present invention and advantages thereof, reference is now made to the following descriptions taken in conjunction with the accompanying drawings in which like reference numbers indicate like features and wherein.

DETAILED DESCRIPTION OF THE INVENTION

Preferred embodiments of the present invention and its advantages are understood by referring to FIGS. 1 through 6 of the drawings, like numerals being used for like and corresponding parts of the various drawings.

Figure 1:
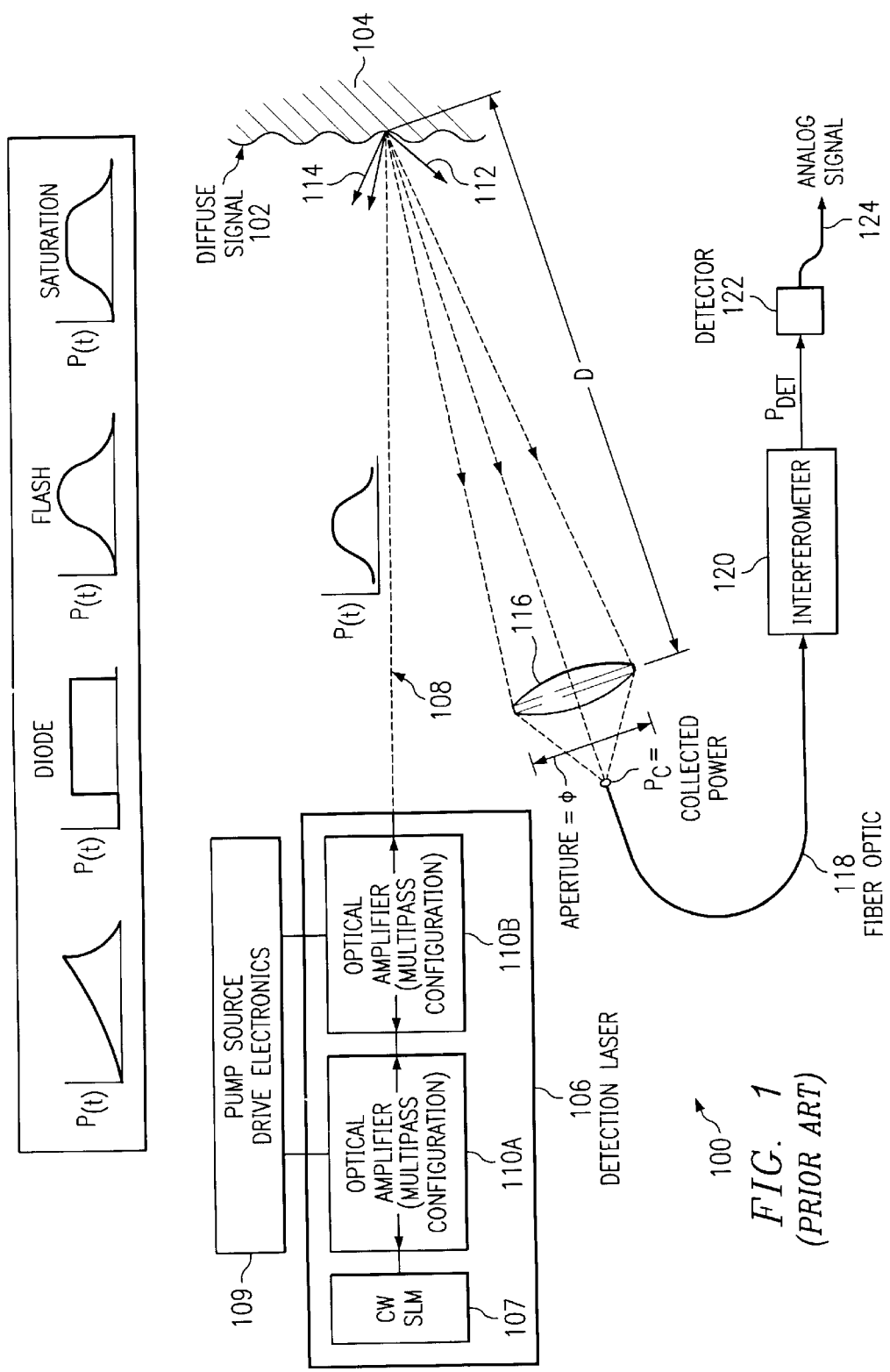
FIG. 1 depicts a known setup for detecting ultrasonic displacements using a detection laser beam.

FIG. 1 illustrates a detection system 100 for detecting ultrasonic displacements 102 at remote target 104. Detection system 100 utilizes a detection laser source 106 to generate a laser beam 108. Detection laser source 106 may incorporate a multi-pass optical amplifier 110, driven by pump source drive electronics 109 to generate laser beam 108 with a power $P_0$. Ultrasonic displacements 102 at remote target 104 modulate, scatter and reflect detection laser beam 108. When detection laser beam 108 interacts with the ultrasonic waves or displacements 102 present at remote target 104, detection laser beam 108 is reflected or scattered as phase-modulated light 112. Phase-modulated light 112 is reflected and scattered in all directions as shown by arrows 114. However, some of the phase-modulated light 112 is captured by collection optics 116. Collection optics 116 direct phase-modulated light 112 via fiber optic 118 into interferometer 120. Interferometer 120 demodulates the phase-modulated light and directs an output into detector 122 which generates an analog signal for processing.

Scattering of the laser beam by the material under test includes all reactions between laser beam 108 and the material under test where laser beam 108 is redirected without otherwise altering the laser beam; furthermore scattering a laser beam by the material under test includes all reactions between the phase modulated light and the material under test with the exception of absorption of the first pulsed laser beam.

Collection optics 116 has an aperture size of $\phi$ and is spaced a distance D from remote target 104. The power of the collected, phase-modulated light as measured at the output of the collector is $P_c$. The power of the collected, phase-modulated light at the input of the interferometer is substantially PC since there is very little transmission loss associated with fiber optic 118. Because the loss in interferometer is minimal, the power of the input signal to the detector ($P_{DET}$) is substantially the same as $P_c$.

The signal-to-noise ratio of detector 122 is directly proportional to the square root of the input power:

$$SNR \propto \sqrt{P_{DET}} \qquad \text{eqn (1)}$$

The above formulas suggest that the SNR can be improved by increasing $P_o$, or $\phi$, or by decreasing D. Increasing the ratio of $\phi/D$ decreases the depth of field of detection system 100, which is undesirable because a decreased depth of field is less flexible.

Alternatively, $P_o$ can be increased. One approach to increase the output of detection laser 106 is to use a shorter pulse width. The pulse of detection laser beam 108, however, must be of a sufficient width to permit detection of ultrasonic displacements, and therefore, decreasing its pulse duration degrades its ability to detect such displacements. A second approach is to amplify the detection laser using a multiple pass optical amplifier. However, the gain of a conventional optical amplifier is dependent upon the power of the input signal.

Where the $P_{DET}$ is given by eqn (2):

$$P_{DET} = \frac{P_0}{4}\left(\frac{\phi}{D}\right)^2 (1-A) \cdot \cos \sigma \cdot \eta \Leftarrow \text{for a diffuse surface}$$

Where
  $P_D$=incident power
  A=absorption
  σ=incident angle
  η=efficiency (mirror losses, fiber losses, etc.)

Figure 2:
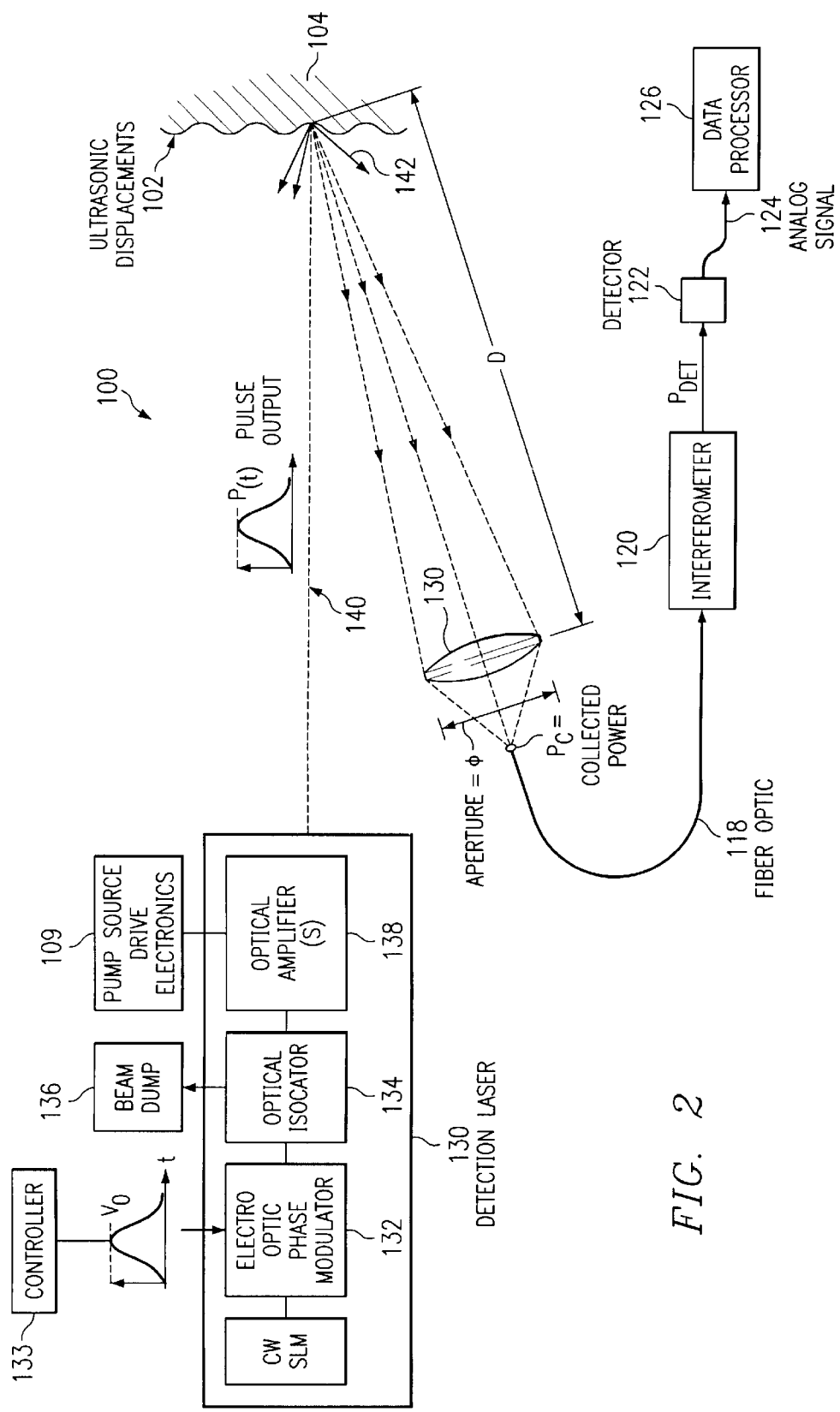
FIG. 2 illustrates shows an embodiment of the present invention using a time-dependent output pulse profile to yield an improved signal-to-noise ratio.

FIG. 2 illustrates a setup for generating and detecting ultrasonic displacements using a detection laser beam similar to that of FIG. 1.

Figure 3A:
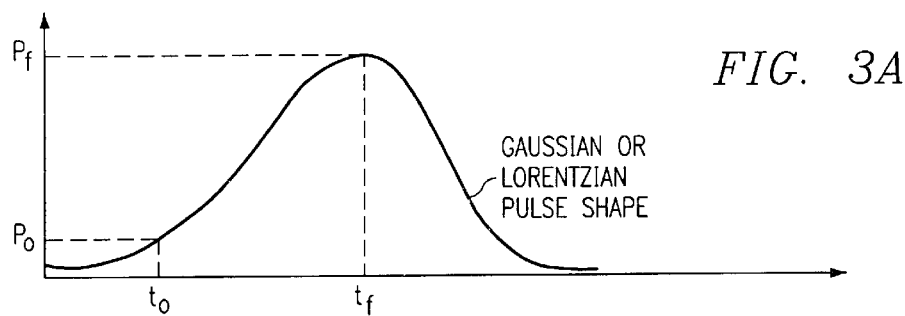
FIG. 3A illustrates a gaussian or lorentzian time-dependent pulse profile.
Figure 3B:
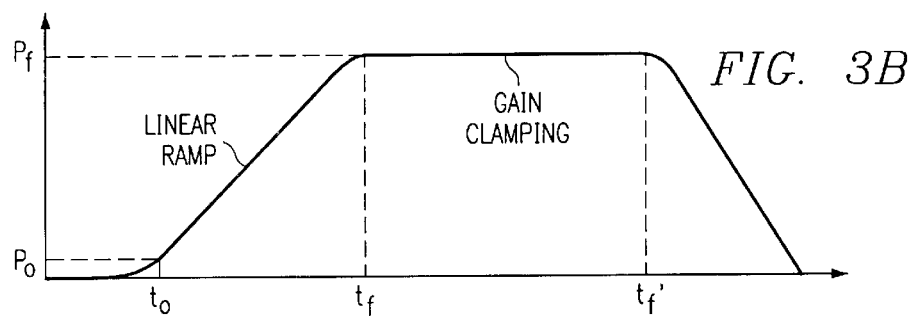
FIG. 3B illustrates a linear ramp to a gain clamped time-dependent pulse profile.
Figure 3C:
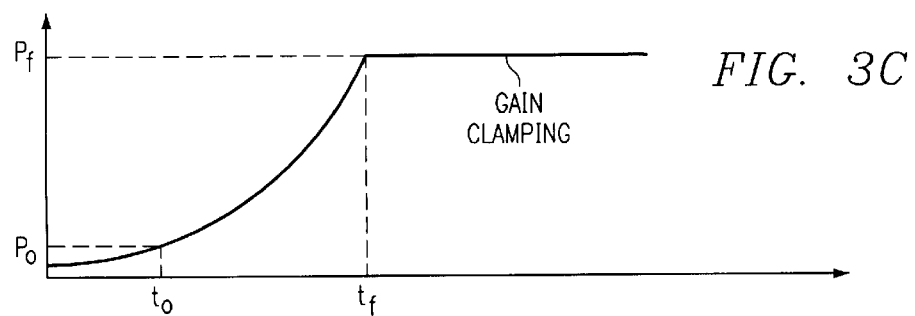
FIG. 3C illustrates an exponential ramp to a gain clamped time-dependent pulse profile.

Detection system 200 utilizes a detection laser 130 to detect ultrasonic displacements 102 on a remote target 104. Detection laser 130 may incorporate an electro optic phase modulator 132 to modulate the laser based on time varying drive voltage. Optical isolator 134 and beam dump 136 to prevent optical feedback into modulator 132. Optical amplifier 138 amplifies the laser beam to produce laser beam 140 with a power $P_{(t)}$. This laser beam 140 can have a time-dependent pulse profile $P_{(t)}$, this pulse profile can be optimized as to improve the signal strength. This time-dependent pulse profile can be optimized to substantially match the attenuation characteristics of remote target 104. Alternatively, a time-dependent pulse profile can be used which does not match the attenuation characteristics of remote target 104 but does provide sufficient variation in the intensity of the pulse profile to alter the dynamic range of the ultrasonic detection process. FIGS. 3A through 3C illustrate potential pulse shapes, including a gaussian or lorentzian pulse shape as shown in FIG. 3A; a linear ramp/gain clamping pulse shape as shown in FIG. 3B; and an exponential pulse shape as shown in FIG. 3C. The present invention need not be limited to the time-dependent pulse profiles described in FIGS. 3A through 3C. Rather, advantageous pulse profiles may be taken such that the signal strength actually increases during the duration of the detection pulse.

The present invention provides a system for detecting ultrasonic displacements at a remote target. The ultrasonic displacements 102 at remote target 104 modulate, scatter and reflect detection laser beam 140, represented by arrows 142 directed away from the remote target 104. When detection laser beam 140 interacts with ultrasonic waves 102, detection laser beam 140 is reflected and/or scattered as phase-modulated light 142. This phase-modulated light contains information representative of the ultrasonic displacements 112 at remote target 104.

Figure 4:
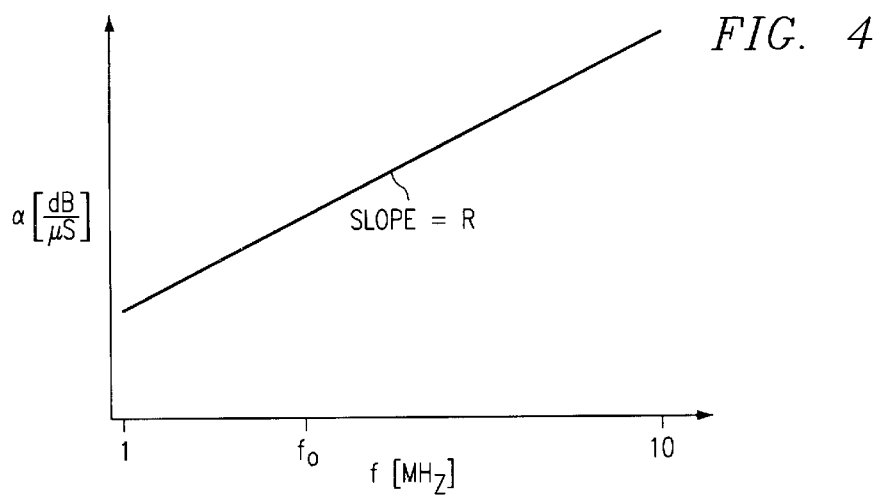
FIG. 4 illustrates a typical plot of frequency dependent material attenuation.

Ultrasonic material displacements 102 are a function of both time and attenuation of the material from which remote target 104 is constructed. This function is shown below in Equation 1.

$$U_{(t)} = U_0 e^{-\alpha_{(f)} t} \qquad \text{(EQN 1)}$$

Where $\alpha_{(f)}$ is the frequency dependent material attenuation as shown in FIG. 4. The measured signal at the detector is given by Equation 2, as follows:

$$S_{(t)} = K \cdot P_{(t)} \cdot U_{(t)} \quad \text{(EQN 2)}$$

Where K is a constant, $P_{(t)}$ is the detection laser power and $U_{(t)}$ is the ultrasonic displacements defined in Equation 1. Over a small frequency range ($\Delta f$), the frequency-dependent material attenuation as shown in FIG. 4 can be approximated by a constant:

$$\alpha_{(f)} \approx \alpha_0$$

Further, the time-dependent pulse profile $P_{(t)}$ can be adjusted such that the pulse profile of the laser 140 substantially matches the attenuation characteristics of the material under test, as shown by the below approximation: $P_{(t)} \approx e^{+\alpha_0 t}$. These approximations associated with the exponential pulse profile of FIG. 3C, yield a measured signal described by Equation 3 below:

$$S_{(t)} = K \cdot U_0 \cdot e^{+\alpha_0 t} \cdot e^{-\alpha_0 t} = K \cdot U_0 \quad \text{(EQN 3)}$$

Here, the pulse profile, $P_{(t)}$, has been made to exactly match the attenuation loss, yielding a constant measured signal strength over time.

Similarly, the pulse profiles provided in FIGS. 3A and 3B allow for an improved signal strength response utilizing a different $P_{(t)}$ function.

More specifically, the present invention provides a system for detecting ultrasonic displacements at a remote target with a laser beam having a time dependent pulse profile. The system and method for improving the dynamic range of laser detected ultrasonic in attenuative materials includes a seed laser light source. This laser source produces a laser which is modulated by an assembly placed in the laser beam's path. The modulated laser has a time-dependent pulse profile. Ultrasonics at the remote target further modulate, reflect and/or scatter the laser beam to produce phase-modulated light. Optics collect this phase modulated light. An interferometer is coupled to the collection optics to demodulate the phase-modulated light and provide an output signal representative of the ultrasonics at the remote target.

A processor may be utilized to process the one output signal of the interferometer to obtain data representative of the ultrasonics.

Another embodiment of the present invention involves matching the time-dependent pulse profile of the detection laser beam to the attenuative properties of the remote target. Alternatively, the time-dependent pulse profile may be varied to increase the signal strength of the detected ultrasonics.

The present invention provides an important technical advantage by extending the dynamic range of a Laser UT system. Previous systems would synchronize the generation of the ultrasonic event with the peak of the detection laser to maximize signal-noise-ratio without regard for potential dynamic range improvements based on exploiting non-uniform illumination profiles, while the present invention provides that the use of time-dependent detection laser illumination profiles can be used to both optimize signal-noise-ratio and extend the dynamic range of the Laser UT systems.

Another technical advantage of the present invention is an extended dynamic range of the system to detect ultrasound in the material under test and improved signal-to-noise ratio for the system due to the time-varying pulse profiles of the detection laser. The time-varying signal can be matched to the attenuative properties of the material, thus optimizing the signal-to-noise ratio of the output signal provided by the detection laser.

Yet another technical advantage of the present invention is the ability to use a detection laser with lower output power allowing the use of smaller collection optics and optical scanners. Additionally, the use of a lower power detection laser reduces the total power applied to the material under test and damage of the material under test. This reduced power requirement is due to the improved signal-to-noise ratio and dynamic range achieved by the application of the time-varying laser pulse.

Although the present invention has been particularly shown and described in detail, it should be understood that various changes, substitutions and alterations can be made hereto without departing from the spirit and scope of the invention as defined in the appended claims.

What is claimed is:

1. A system for detecting ultrasonic displacements in a material under test, comprising:
   a seed laser light source that provides a first laser beam having a path of propagation;
   a modulator assembly placed in said path of said first laser beam operable to provide an output pulse having a time-dependent pulse profile;
   an ultrasonic induction system which induces ultrasonic displacements in the material under test;
   a detection system which applies said output pulse of said first laser beam to the material under test in order to detect the ultrasonic displacements and generate at least one output signal; and
   a data processor to process said at least one output signal of said detection system to obtain data representative of said ultrasonic displacements.

2. The system of claim 1, wherein said modulator assembly further comprises an electro-optic crystal driven by a signal processor for providing said output pulse with a time-dependent pulse profile.

3. The system of claim 1, wherein said time-dependent pulse profile substantially matches an attenuation characteristic of the material under test.

4. The system of claim 1, wherein said time-dependent pulse profile provides sufficient variation in intensity to alter a dynamic range of said detection system.

5. The system of claim 1, wherein the ultrasonic induction system further comprises:
   a second laser to generate a second pulsed laser beam wherein said second pulsed laser beam induces ultrasonic displacements in the material under test.

6. The system of claim 5, wherein said second pulsed laser beam is applied coaxially with said first pulsed laser beam to the material under test and a profile of said second pulsed laser beam is synchronized with said time-dependent pulse profile.

7. The system of claim 1, further comprising at least one optical isolation assembly placed in said path of propagation of said first laser beam in order to prevent reflected laser light feedback into said seed laser light source.

8. The system of claim 7, further comprising at least one optical beam dump positioned with respect to said at least one optical isolation assembly in order to absorb reflected laser light feedback isolated by the optical isolation assembly.

9. The system of claim 1, further comprising at least one laser light amplification assembly placed in said path of propagation of said first laser beam for amplifying said first laser beam.

10. The system of claim 1, wherein said data processor converts at least one analog output signal of said detection system into at least one digital signal to obtain data representative of ultrasonic displacements in the material under test.

11. A system for detecting ultrasonic displacements in a material under test comprising:
- a seed laser light source that provides a first laser beam having a path of propagation;
- a modulator assembly placed in said path of propagation operable to provide for time-varying of output pulse having a time-dependent pulse profile;
- a controller operable to direct said modulator assembly;
- at least one optical isolation assembly placed in said path of propagation that prevents reflected laser light feedback into said seed laser light source;
- at least one optical beam dump positioned with respect to said at least one optical isolation assembly in order absorb reflected laser light feedback isolated by said optical isolation assembly;
- at least one laser light amplification assembly placed in said path of propagation in order to amplify said first laser beam;
- an ultrasonic induction system which induces ultrasonic displacements into the material under test;
- a detection system which applies said output pulse to the material under test, detects ultrasonic displacements in the material under test, and generates at least one output signal; and
- a data processor to process said at least one output signal in order to obtain data representative of said ultrasonic displacements in the material under test.

12. The system of claim 11, wherein said time-dependent pulse profile substantially matches an attenuation characteristic of the material under test.

13. The system of claim 11, wherein an intensity of said time-dependent pulse profile alters a dynamic range of said detection system.

14. The system of claim 11, wherein said modulator assembly further comprises an electro-optic crystal driven by a processor to provide said time-dependent pulse profile.

15. The system of claim 11, wherein said ultrasonic induction system further comprises:
- a second laser source that generates a second pulsed laser beam that induces ultrasonic displacements when applied to the material under test.

16. The system of claim 11, wherein said ultrasonic induction system further comprises:
- a second laser source that generates a second pulsed laser beam that induces ultrasonic displacements in the material under test, and wherein said second pulsed laser beam is applied coaxially with said first pulsed laser beam to the material under test, and wherein a pulse profile of said second pulsed laser beam is synchronized with said time-dependent pulse profile of said first laser beam.

17. The system of claim 11, wherein said data processor converts said at least one output signal of said detection system into at least one digital signal and processes the at least one digital signal to obtain data representative of ultrasonic displacements in the material under test.

18. The system of claim 11, wherein said data processor processes said at least one analog output signal of said detection system in order to determine a location of a flaw or discontinuity within the material under test.

19. A method for detecting ultrasonic displacements in a material under test, comprising the steps of:
- generating the ultrasonic displacements in the material under test;
- generating a first laser pulse having a time-dependent pulse profile;
- applying said first laser pulse to the material under test;
- detecting the laser light of said first laser pulse modulated by the ultrasonic displacements at the material under test; and
- converting said modulated laser light into at least one output signal containing data representative of the ultrasonic displacements in the material under test.

20. The method of claim 19, wherein said step of generating a first laser pulse further comprises the steps of:
- generating a first laser beam from a seed laser light source, wherein said first laser beam has a path of propagation; and
- modulating said first laser beam with a modulator assembly placed in said path of propagation of said first laser beam, said first laser pulse having said time-dependent pulse profile.

21. The method of claim 19, further comprising amplifying said first laser pulse with at least one laser light amplification assembly.

22. The method of claim 20, wherein said step of modulating said first laser beam comprises:
- modulating said first laser beam with an electro-optic phase modulator; and
- using a controller to drive the electro-optic phase modulator to produce said time-dependent pulse profile.

23. The method of claim 22, wherein said controller drives said modulator to produce a profile for said time-dependent pulse profile selected from the group consisting of:
- a gaussian or lorentzian pulse shape;
- a flat profile with a linear ramp pulse shape; and
- an exponential gain pulse shape.

24. The method of claim 19, wherein said at least one signal is an optical signal, and wherein the step of converting the at least one signal into data representative of the ultrasonic displacements in the material under test further comprises:
- converting the at least one optical signal into at least one analog signal;
- converting the at least one analog signal into at least one digital signal; and
- converting the at least one digital signal into data representative of the ultrasonic displacements in the material under test.

25. The method of claim 19 further comprising processing said output signal to determine a location of flaws or any discontinuities at the target.

* * * * *